United States Patent [19]

Hecker

[11] Patent Number: 4,513,140

[45] Date of Patent: Apr. 23, 1985

[54] 2-AMINO-4,5-DIHYDRO-1H-IMIZOLE-1-CARBOXANILIDES

[75] Inventor: Leonard R. Hecker, Ambler, Pa.

[73] Assignee: McNeilab, Inc., Fort Washington, Pa.

[21] Appl. No.: 514,541

[22] Filed: Jul. 18, 1983

Related U.S. Application Data

[62] Division of Ser. No. 316,601, Oct. 30, 1981, abandoned.

[51] Int. Cl.³ ............................................ C07D 233/46
[52] U.S. Cl. .................................................... 548/315
[58] Field of Search ........................................ 548/315

[56] References Cited

U.S. PATENT DOCUMENTS

| | | | |
|---|---|---|---|
| 4,229,462 | 10/1980 | Rasmussen | 424/273 R |
| 4,238,497 | 12/1980 | Black et al. | 424/273 R |
| 4,239,768 | 12/1980 | Rasmussen | 424/273 R |

FOREIGN PATENT DOCUMENTS 741948  5/1970  Belgium .

*Primary Examiner*—Jane T. Fan
*Attorney, Agent, or Firm*—David J. Levy

[57] ABSTRACT

Novel 2-amino-4,5-dihydro-1H-imidazole-1-carboxanilides, which are made by reacting 2-amino-4,5-dihydroimidazole with an aryl isocyanate, are made stable to rearrangement when converted to acid addition salt form, and are useful either as antihypertensive agents and/or antisecretary agents, as well as being intermediates to prepare known pharmacologically active N-aryl-N'-(4,5-dihydro-1H-imidazol-2-yl)ureas.

1 Claim, No Drawings

2-AMINO-4,5-DIHYDRO-1H-IMIZOLE-1-CARBOXANILIDES

This is a division of application Ser. No. 316,601, filed Oct. 30, 1981, now abandoned.

This invention is concerned with novel compounds and a process for their production, the compounds being 2-amino-4,5-dihydro-1H-imidazole-1-carboxanilides (I).

The compounds of the present invention have the formula I

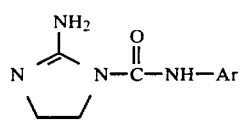

wherein Ar represents phenyl substituted with from 0 to 3 substituents independently selected from fluoro, chloro, bromo, methyl, ethyl, methoxy, ethoxy, trifluoromethyl and methylthio, and include the pharmaceutically acceptable salts thereof.

In the most preferred compounds, Ar represents

wherein n is an integer from 1 to 2 and each R is independently selected from the group of chloro, bromo, methyl, ethyl, methoxy, and trifluoromethyl.

The compounds of the present invention (I) either have a pharmacological utility themselves or are useful as intermediates to prepare known compounds having pharmacological activity. Various of the compounds (I) have utility as antihypertensive agents and/or as antisecretory agents. The compounds (I) can be used as intermediates to prepare pharmacologically active N-aryl-N'-(4,5-dihydro-1H-imidazol-2-yl) ureas (IV). The latter compounds are disclosed in Rasmussen, U.S. Pat. No. 4,229,462 (as antihypertensive agents) and in Rasmussen, U.S. Pat. No. 4,239,768 (for relieving the symptoms associated with irritable bowel syndrome) and also in the copending patent application of Rasmussen, U.S. Ser. No. 156,900, filed June 6, 1980, entitled "N-(Substituted Phenyl)-N'-(2-Imidazolidinylidene) Ureas", which is a CIP of said U.S. Pat. No. 4,229,462, assigned to the Assignee of the instant application, and is intended to be incorporated herein by reference.

The compounds of the present invention (I) are made by the process depicted in the following reaction scheme, which also depicts how they are used as intermediates.

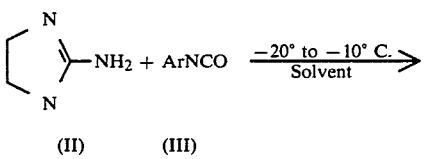

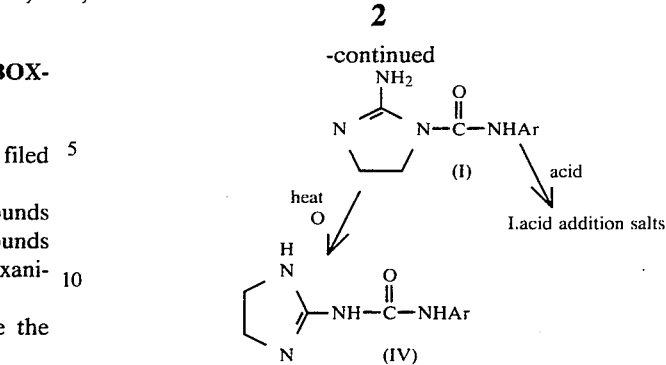

In the above reaction scheme and throughout the specification and claims, Ar has the definitions previously given. It has been surprisingly found that reaction of 2-amino-4,5-dihydroimidazole (II) with aryl isocyanates (III) in suitable organic solvents generally at temperatures of $-10°$ to $-20°$ C. leads to formation of the subject carboxanilides (I) generally as the major product. Carboxanilides (I) in free base form are found to rearrange readily at temperatures of about 20° to 110° C. to N-aryl-N'-(4,5-dihydro-1H-imidazol-2-yl) ureas (IV). In order to minimize rearrangement of free base I, isolation of I is carried out rapidly at temperatures of about 0° to 10° C. and converted to acid addition salt form by treatment with strong mineral acids, such as HCl (preferred), $H_2SO_4$, HBr, $HNO_3$, $H_3PO_4$, HI and the like, or with strong organic acids such as methane-, ethane-, benzene-, p-toluene-, $\alpha$- and $\beta$-naphthylene-, and the like sulfonic acids. In acid addition salt form, compounds (I) are stable to rearrangement and can be purified by techniques known in the art such as recrystallization from organic solvents, $H_2O$, and $H_2O$ common acid mixtures, such as $H_2O$—HCl.

After conversion of I in acid addition salt form to the corresponding free base form, the rearrangement of I to N-aryl-N'-(4,5-dihydro-1H-imidazol-2-yl) ureas (IV) can be readily followed by nuclear magnetic resonance spectroscopy, characterized by the disappearance of the typical $A_2X_2$ pattern [multiplets at about 3.7 and 4.3 ppm ($\delta$)] and appearance of an $A_2B_2$ singlet at about 3.7 ppm ($\delta$). The rearrangement has been observed in solutions of organic solvents such as toluene, chloroform, N,N-dimethylformamide, THF and the like at temperatures of about 20° to 110° C. The rearrangement has also been observed to occur slowly in the solid state at ambient temperatures and rapidly at elevated temperatures, including the melted state.

Tautomeric structures for I can be written, thus,

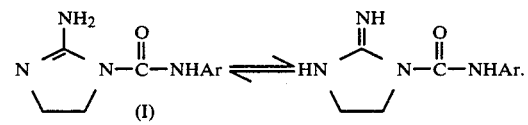

Certain of the aforementioned salts form hydrates of varying composition. It is intended that said hydrates be included within the scope of this invention.

METHODS OF PREPARATION

In a preferred method ("Method A") an acid addition salt of 2-amino-2-imidazoline (II) is either suspended in or dissolved in an ether-like solvent such as THF (preferred), 1,4-dioxane, 1,2-dimethoxyethane and the like, and stirred with an equimolar amount of 50 percent sodium hydroxide solution in order to generate free base II. To the resulting mixture, containing about 1.5 molar equivalents of free base II is added in situ a drying agent such as anhydrous sodium sulfate (preferred), anhydrous potassium carbonate and the like. After stirring, the drying agent may be removed by filtration or, alternatively, remain in situ. The mixture containing II is then cooled to a temperature of about 20° to −35° C. (−10° to −20° C. preferred) and treated dropwise, generally in an inert atmosphere such as nitrogen or argon, with about one molar equivalent of an appropriate aryl isocyanate (III) to produce the desired 2-amino-4,5-dihydro-1H-imidazole-1-carboxanilides (I). After sufficient reaction time, the solvent is removed in vacuo at temperatures generally less than 10° C. and the residue converted to a stable acid addition salt of I.

Purification of the acid addition salt is performed by techniques known in the art.

In a second general, but less preferred method ("Method B"), free base II, about 2 molar equivalents, is first generated from its HI (preferred) or other acid addition salt by reaction with an equivalent amount of lithium hydride in an anhydrous polar aprotic solvent such as dry DMF (preferred), hexamethylphosphorictriamide, and the like in an inert atmosphere such as nitrogen or argon. The resulting mixture, containing about 2 molar equivalents of free base II, is cooled to about 20° to −35° C. (−10° to −20° C. preferred) and treated dropwise with about one molar equivalent of the appropriate aryl isocyanate (III) in the same solvent while maintaining a temperature of about 20° to −35° (−10° to −20° C. preferred) to produce the desired 2-amino-4,5-dihydro-1H-imidazole-1-carboxanilides (I).

Although carboxanilides I are formed in the reaction mixture at temperatures as high as ambient, the rate of rearrangement to the ureas IV is more rapid under these conditions.

PHARMACOLOGY

I. As Antihypertensive Agents

The subject compounds have been shown to have useful antihypertensive activity (see Table I). Interestingly, the 2,6-disubstituted carboxanilides (Examples 1, 5) show significantly less antihypertensive activity than their corresponding rearranged products IV, suggesting that rearrangement of I to IV in vivo does not occur with sufficient rapidity to form the more active species. Conversely, in certain instances, for example 4-tolyl, 4-Cl, the 1-carboxanilides show more potent antihypertensive activity than do their corresponding N-aryl-N'-(4,5-dihydro-1H-imidazol-2-yl) ureas.

The antihypertensive compounds of the present invention do not show an increase in heart rate, but either a lowering or no significant change of heart rate. An agent which has an antihypertensive effect without increasing but rather maintaining or decreasing heart rate, is considered most useful for beneficially treating a hypertensive subject. The extent to which a compound possesses these properties may be primarily determined in the antihypertensive test hereinafter described.

RODENT ANTIHYPERTENSIVE SCREEN

This test evaluates compounds for effects on arterial pressure and heart rate. In this test, the arterial pressure of adult spontaneously hypertensive rats (Charles River) is monitored directly via an aortic cannula. Rats are anesthetized with an inhalation anesthetic (methoxyflurane). The left carotid artery is isolated and cannulated. The tip of the cannula is advanced to the aorta and the cannula is exteriorized behind the neck at the level of the scapula. Animals are placed in individual cages and allowed to recover from the anesthetic and are kept unrestrained. The arterial cannula is connected to the pressure transducer which is attached to the recorder. Heart rate is determined from the arterial pressure recording. The test compounds are administered either orally (p.o.) by gavage or by intraperitoneal (i.p.) injection. The arterial pressure and heart rate are monitored for a minimum of 24 hours. A test compound is considered to be active as an antihypertensive agent if the mean arterial pressure (MAP) indicates a fall of >15 mm of Hg. Each animal serves as his own control.

The results of this test employing at least 3 rats per dose level for each compound and performed with various compounds of the present invention are shown in Table I. The results seen in Table I show that the compounds of the present invention and their salts possess not only the beneficial antihypertensive property but also the desirable property of maintaining or lowering heart rate.

The antihypertensive compounds of the present invention are useful for treating hypertension (high blood pressure) by administering to subjects in need of treatment, a therapeutically-effective hypertension-reducing amount of said compounds or their pharmaceutically-acceptable salts as active agent. The active agents may be administered with or without carrier in the amounts hereinafter set forth. A preferred method of administration is by the use of pharmaceutical compositions in unit dosage form as described below.

The operable ranges for carrying out the treatment is the administration, orally or parenterally, of from about 5 mg. to about 500 mg. of said antihypertensive compound in dosage unit form. While the therapeutic method is most useful for human subjects, it may also be employed for other mammals. Operable amounts are generally within the range of from about 0.5 to 100 mg/kg of body weight.

TABLE I

| | | Antihypertensive and cardiac rate determinations Spontaneously hypertensive rat | | | |
|---|---|---|---|---|---|
| Example | Ar | Dose (mg/kg p.o.) | Max. decr. in MAP (mm Hg) | Duration (hrs) | Effect on heart rate (beats/min) |
| 9 | 2,4-Cl$_2$Ph | 35 | 33 | 2.0 | −49 |
| 10 | 2,3-Cl$_2$Ph | 35 | 19 | 1.0 | −66 |
| 6 | 3,5-Cl$_2$Ph | 35 | 22 | 1.0 | −21 |
| 5 | 2,6-(CH$_3$)$_2$Ph | 35 | 23 | 1.0 | −27 |
| 7 | 2,5-Cl$_2$Ph | 35 | 37 | 1.0 | −48 |
| 2 | 4-CH$_3$Ph | 35 | 54 | 6.0 | −162 |
| 3 | 2-ClPh | 35 | 35 | 2.0 | −77 |
| 1 | 2,6-Cl$_2$Ph | 35 | 32 | 0.5 | −48 |

TABLE I-continued $\underset{N}{\overset{NH_2}{\bigwedge}} \underset{\underset{\diagdown\underline{\quad}\diagup}{N}}{\overset{O}{\underset{\|}{-C-}}}NHAr \cdot HCl$

| | | | Antihypertensive and cardiac rate determinations Spontaneously hypertensive rat | | |
|---|---|---|---|---|---|
| Example | Ar | Dose (mg/kg p.o.) | Max. decr. in MAP (mm Hg) | Duration (hrs) | Effect on heart rate (beats/min) |
| 11 | 3-ClPh | 35 | 20 | 0.5 | −26 |
| 8 | 3,4-Cl$_2$Ph | 35 | 44 | 2.0 | −68 |
| 12 | 2,4,6-Cl$_3$Ph | 35 | 18 | 0.5 | −39 |
| 14 | 4-CF$_3$Ph | 35 | 50 | 5.0 | −98 |
| 25 | 2-CF$_3$Ph | 35 | 32 | 0.5 | −21 |
| 26 | 3-CF$_3$Ph | 35 | 24 | 2.0 | −71 |
| 20 | 4-OCH$_3$Ph | 35 | 16 | 1.0 | −38 |
| 27 | 4-ClPh | 35 | 41 | 15 | −66 |
| 4 | 3,4-(OCH$_3$)$_2$Ph | 100 | 47 | 11 | −215 |

II. As Antisecretory Agents

In addition to antihypertensive activity, some of the subject 1-carboxanilides, e.g., 2,6-(CH$_3$)$_2$Ph, 4-CH$_3$Ph, 3-CF$_3$Ph, and others have exhibited useful antisecretory activity as shown in Table II.

The principal antisecretory screen is the acute gastric fistula rat test which is carried out as follows:

Female Sprague-Dawley rats are used for this study. The weights range from 125–250 gms; however, weights in any given test have a range of ±20 gms. The rats are fasted 24 hours before testing, water is given ad lib. At the time of fasting, the rats are placed in individual cages with wide mesh bottoms. This eliminates the problem of cannibalism and coprophagia.

On the day of testing, the rats are weighed beforehand to determine the weight range and to allow for even distribution.

Surgery is carried out under light ether anesthesia. As soon as the rat is anesthetized, its teeth are removed using a small pinch pliers. A midline incision is made on the abdomen about 1½ cm long and the stomach is exposed. If, at this point, the stomach is filled with food or fecal material, the rat is discarded except for orally administered rats. In this case, the stomach contents are gently squeezed into the duodenum.

Using a 4-0 polyester fiber suture, a purse string stitch is placed on the fundic portion of the stomach taking care to avoid any blood vessels in the area. A small nick is made into the stomach in the center of the purse string and a cannula, consisting of a small vinyl tube with a flange on one end, is put into the stomach and the purse string is closed tightly around the flange. Immediately following this, the rat is dosed intraduodenally using a volume of 0.5 ml per 100 gm body weight. The abdominal wall and skin are closed simultaneously with three to four 18 mm wound clips. The rat is then placed in a box containing a longitudinal slit which allows the cannula to hang freely and the rat is able to move about unencumbered.

At the completion of the procedure, the time is marked 0 minutes. The rat is allowed to stabilize for 30 minutes, at which time the collection tube is discarded and replaced with a clean collection tube to receive the gastric juice. Only a one-hour collection is made for a screening study. In evaluation studies, one- and two-hour collections are made. At the end of the study, the cannula is pulled out and the rat is sacrificed.

The gastric contents collected are drained into a centrifuge tube and centrifuged to pack down the sediment. The volume is read and a 1 ml aliquot of the supernatant is put into a beaker containing distilled water and titrated to pH 7 using 0.01N NaOH.

Mean values are determined for volume, titratable acid and total acid output where volume equals total ml of gastric juice minus sediment, titratable acid (mEq/l) equals amount of 0.01N NaOH needed to titrate the acid to pH 7 times 10 and total acid output equals titratable acid times volume. Results are reported in percent inhibition over control values.

In studies using oral administration, the drugs are dosed in a volume of 1 ml per 100 gm body weight one hour before surgery (pretreatment equals 90 minutes). In subcutaneous studies, the drug may be given immediately after the surgical procedure (pretreatment equals 30 minutes) or after the 30-minute stabilization period when the collection tube is changed (pretreatment time equals 0 minutes). The volume used in subcutaneous studies is 0.2 ml per 100 gm body weight.

TABLE II $\underset{N}{\overset{NH_2}{\bigwedge}} \underset{\underset{\diagdown\underline{\quad}\diagup}{N}}{\overset{O}{\underset{\|}{-C-}}}NHAr \cdot HCl$

| | | | (Antisecretory Determinations) Gastric fistula rat | |
|---|---|---|---|---|
| Example | Ar | Dose (mg/kg I.D.) | % Inhibition of gastric secretion | (mg/kg p.o.) ED$_{50}$ (1 hr) |
| 17 | 2-C$_2$H$_5$—6-CH$_3$Ph | 20 | 91 | 24.48 |
| 16 | 2,6-Br$_2$Ph | 20 | 64 | — |
| 9 | 2,4-Cl$_2$Ph | 20 | 71 | 14.8 |
| 10 | 2,3-Cl$_2$Ph | 20 | 70 | — |
| 6 | 3,5-Cl$_2$Ph | 20 | 75 | 22.3 |
| 5 | 2,6-(CH$_3$)$_2$Ph | 20 | 88 | — |
| 2 | 4-CH$_3$Ph | 20 | 99 | 4.6 |
| 3 | 2-ClPh | 20 | 82 | — |
| 1 | 2,6-Cl$_2$Ph | 20 | 62 | — |
| 11 | 3-ClPh | 20 | 77 | 14.2 |
| 8 | 3,4-Cl$_2$Ph | 20 | 96 | 24.8 |
| 12 | 2,4,6-Cl$_3$Ph | 20 | 97 | — |
| 15 | 2-Cl—6-CH$_3$Ph | 20 | 77 | — |

TABLE II-continued

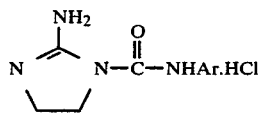

| | | | (Antisecretory Determinations) Gastric fistula rat % Inhibition | |
|---|---|---|---|---|
| Example | Ar | Dose (mg/kg I.D.) | of gastric secretion | (mg/kg p.o.) ED$_{50}$ (1 hr) |
| 14 | 4-CF$_3$Ph | 20 | 70 | 35.5 |
| 19 | 3-OCH$_3$Ph | 20 | 74 | — |
| 26 | 3-CF$_3$Ph | 20 | 99 | — |
| 23 | Ph | 20 | 92 | — |
| 24 | 2-CH$_3$Ph | 20 | 65 | — |
| 27 | 4-ClPh | 20 | 95 | 29.3 |

METHOD A
2-Amino-N-aryl-4,5-dihydro-1H-imidazol-1-carboxamide Hydrochloride Salts (A General Method)

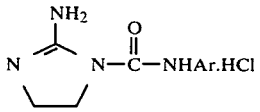

A suspension of 2-amino-1-imidazolidine monohydroiodide in tetrahydrofuran (THF) is treated with an equimolar amount of 50% sodium hydroxide solution and stirred for a period of about 0.5 hour. Anhydrous sodium sulfate is added to remove water and the inorganics can be removed by filtration or allowed to remain in situ. The solution containing 2-amino-1-imidazolidine free base is cooled to about −25° C. and a solution of about 0.5 equivalents of the appropriate aryl isocyanate in THF is added dropwise over about a 2.5-hour period while stirring under an atmosphere of nitrogen. The clear solution is stirred an additional period of time (about 1 hour) and the solvent removed in vacuo keeping the temperature at least than 10° C. (keeping the temperature of the free base forms below 10° C. is critical due to the relative ease of rearrangement of these substances to their isomeric form IV). The pot residue is partitioned between chloroform and water and the organic phase is separated and dried with anhydrous potassium carbonate. The drying agent is removed by filtration and the filtrate is rapidly treated with excess methanolic hydrogen chloride. Evaporation in vacuo yields the crude salt of I which is recrystallized from a solvent mixture such as methanol-ether to yield the pure product, as crystalline solids.

METHOD B
2-Amino-N-aryl-4,5-dihydro-1H-imidazol-1-carboxamide Hydrochloride Salts (A General Method)

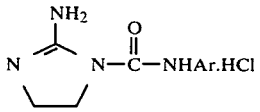

A suspension of 75% lithium hydride in dry N,N-dimethylformamide is treated with a solution of one equivalent of 2-amino-1-imidazolidine monohydroiodide in dry DMF dropwise while stirring in an atmosphere of nitrogen. The rate of addition is regulated so that the temperature does not exceed +25° C. Stirring is continued until the mixture becomes homogeneous (about 1 hour) and the mixture cooled to −20° C. A solution of about 0.5 to 0.75 equivalents of the appropriate aryl isocyanate in dry DMF is added dropwise over about a 2-hour period while maintaining a temperature of about −20° C. The reaction mixture is poured onto ice and treated with excess 10% hydrochloric acid. Insoluble by-products are removed by filtration and the filtrate treated with potassium carbonate to pH >9. The resulting free base is filtered and washed with water and immediately (it is critical to convert the free base to its hydrochloride salt as rapidly as possible to minimize rearrangement to the 2-isomer IV) converted to its hydrochloride salt in methanolic hydrogen chloride. Ether is added to precipitate the crude product. Recrystallization from methanol-ether (other suitable solvents or combinations of solvents, e.g., 2-propanol, MeOH/2-propanol, etc., may be used) generally affords the pure product as a white crystalline solid.

EXAMPLE 1
2-Amino-N-(2,6-dichlorophenyl)-4,5-dihydro-1H-imidazole-1-carboxamide Monohydrochloride

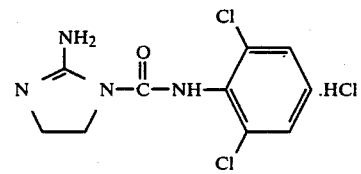

A suspension of 1.06 g (0.10 mole) of 75% lithium hydride in 35 ml of dry DMF was treated with a solution of 21.3 g (0.10 mole) of 2-iminoimidazolidine.HI in 20 ml of dry DMF dropwise with stirring under nitrogen so that the temperature did not exceed +25° C. Stirring was continued until all was homogeneous (1 hour), then the mixture was cooled to −20° C. and a solution of 14.1 g (0.075 mole) of 2,6-dichlorophenyl isocyanate in 15 ml of dry DMF was added dropwise over a 2-hour period. Excess aqueous 10% HCl was added to the DMF solution (pH <3) and the mixture poured onto 1 l of ice/H$_2$O, stirred well and filtered, some insoluble material. The filtrate was basified with solid K$_2$CO$_3$ to pH >9 and the resulting free base was filtered and washed thoroughly with water. The crude free base was immediately suspended in methanol and treated with excess methanolic HCl giving a solution. Ether was added to well past the cloud point and 3.2 g of crude hydrochloride salt was filtered off. The original aqueous filtrate yielded a second crop (5.5 g) of free base while standing for two days at room temperature. This was treated in the same way with methanolic HCl to yield a second crop of crude hydrochloride salt. The combined crops were recrystallized twice from methanol/2-propanol and dried in vacuo at room temperature to yield analytically pure product, 6.5 g (30%) m.p. 200°–202° C. dec. to a new solid which melts at 230°–232° C.

Anal. Calc'd for $C_{10}H_{10}N_4OCl_2 \cdot HCl$: C, 38.80; H, 3.58; N, 18.10. Found: C, 38.53; H, 3.62; N, 17.99.

EXAMPLE 2

2-Amino-4,5-dihydro-N-(4-methylphenyl)-1H-imidizole-1-carboxamide Monohydrochloride Hydrate (4:1)

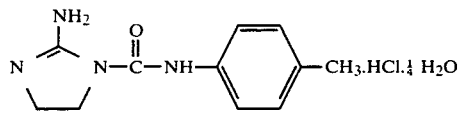

A stirred suspension of 0.954 g (0.12 mole) of lithium hydride in 100 ml of dry DMF was cooled to 0° C. under an atmosphere of nitrogen and treated dropwise with a solution of 25.5 g (0.12 mole) of 2-iminoimidazolidine hydroiodide in 100 ml of dry DMF. The mixture was stirred for 0.5 hour at 0° C. then allowed to warm to room temperature for 1.5 hours. The resulting clear solution was cooled to −20° C. and a solution of 10.65 (0.08 mole) of 4-tolyl isocyanate in 100 ml of dry DMF was added dropwise over a 2-hour period. The mixture was stirred at −20° C. for 3 hours then allowed to warm to 0° C. and poured onto 1 l of ice/H$_2$O with stirring. A white precipitate formed and as filtered off and washed thoroughly with water. The precipitated free base was suspended in methanol and treated with excess methanolic HCl to pH <2. A white solid precipitated, which was filtered off and the filtrate was concentrated to dryness in vacuo. Water (40 ml) was added to the residue and an additional batch of insoluble material was filtered off. The filtrate was treated with charcoal and filtered again. The aqueous solution (pH <3) was treated with solid potassium carbonate to yield nearly pure free base as a white crystalline solid. This was dissolved in fresh methanol and treated with methanolic HCl followed by excess ether to yield nearly pure hydrochloride salt. The crude solid was recrystallized twice from MeOH/2-PrOH to yield pure product, m.p. 218°–219° C. (dec).

Anal. Calc'd for $C_{11}H_{14}N_4O \cdot HCl \cdot \frac{1}{4}H_2O$: C, 50.97; H, 6.03; N, 21.61; H$_2$O, 1.74 Found: C, 50.88; H, 6.12; N, 21.62; H$_2$O, 2.07.

EXAMPLE 3

2-Amino-N-(2-chlorophenyl)-4,5-dihydro-1H-imidazole-1-carboxamide Monohydrochloride

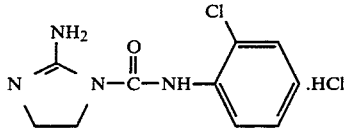

A suspension of 1.60 g (0.15 mole) of 75% lithium hydride in 50 ml of dry DMF was treated with a solution of 31.9 g (0.15 mole) of 2-iminoimidazolidine hydroiodide in 25 ml of dry DMF. The temperature was maintained at 20° C. with external cooling. The mixture was stirred under an atmosphere of nitrogen until it became homogeneous, then cooled to 0° C. while a solution of 11.52 g (0.075 mole) of 2-chlorophenyl isocyanate in 25 ml of dry DMF was added dropwise over a 1-hour period. Stirring at 0° to +5° C. was continued for an additional 2.5 hours. The clear reaction mixture was then poured onto 500 g of ice and acidified with 10% HCl to pH 3. A small amount of insoluble material was filtered off and the filtrate basified with solid K$_2$CO$_3$ (cooling). The aqueous mixture was allowed to crystallize in the refrigerator for 1 hour and filtered to yield crude free base. The crude material was dissolved in methanol with methanolic HCl and diluted with ether to yield 10.8 g of crude hydrochloride salt, mp 200°–202° C. (dec). Two recrystallizations from methanol/2-propanol yielded the pure product, a white solid, m.p. 209°–211° C., 9.69 g (47%), which was dried in vacuo at room temperature.

Anal. Calc'd for $C_{10}H_{14}N_4OCl \cdot HCl$: C, 43.65; H, 4.40; N, 20.36; Found: C, 43.65; H, 4.47; N, 20.35.

EXAMPLE 4

2-Amino-N-(3,4-dimethoxyphenyl)-4,5-dihydro-1H-imidazole-1-carboxamide Monohydrochloride Hydrate (4:1)

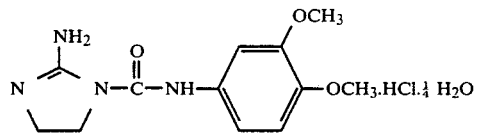

The title compound was prepared by Method A. The crude salt was purified by recrystallization from MeOH/CHCl$_3$ to yield the purified product, a white solid, m.p. 204.5°–205.5° C. (dec).

Anal. Calc'd for $C_{12}H_{16}N_4O \cdot HCl \cdot \frac{1}{4}H_2O$: C, 47.22; H, 5.78; N, 18.35; H$_2$O, 1.48; Found: C, 47.15; H, 5.70; N, 18.39; H$_2$O, 1.21.

EXAMPLE 5

2-Amino-N-(2,6-dimethylphenyl)-4,5-dihydro-1H-imidazole-1-carboxamide Monohydrochloride

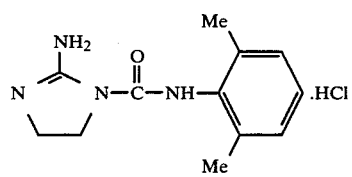

The title compound was prepared by Method B. The crude salt was purified by recrystallization from MeOH/2-PrOH to yield the purified product, a white solid, m.p. 203°–205° C. (m.p. observed at 203°–205° C., then a new solid forms which melts with bubbling at 280° C.).

Anal. Calc'd for $C_{12}H_{16}N_4O \cdot HCl$: C, 53.63; H, 6.38; N, 20.85; Found: C, 53.61; H, 6.51; N, 20.62.

EXAMPLE 6

2-Amino-N-(3,5-dichlorophenyl)-4,5-dihydro-1H-imidazole-1-carboxamide Monohydrochloride Hydrate (16:1)

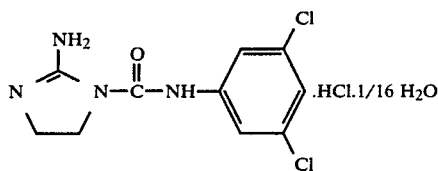

A suspension of 1.7 g (0.213 mole) of lithium hydride in 100 ml of dry DMF was treated under $N_2$ with a solution of 45.37 g (0.213 mole) of 2-iminoimidazolidine monohydroiodide in 60 ml of dry DMF dropwise so that temperature did not exceed +30° C. The mixture was stirred for 2 hours, then cooled to −35° C. and a solution of 20 g (0.106 mole) of 3,5-dichlorophenyl isocyanate in 50 ml of dry DMF was added dropwise over a ½-hour period. Stirring at −35° to −30° C. was maintained for 5 hours. The temperature was allowed to rise to 0° C. and the mixture stirred for 2 hours, kept cold in ice and 10% HCl was added to pH <3, forming a slurry of white solid which was poured onto 1 l of ice/$H_2O$, stirred, and filtered to remove insoluble materials. The filtrate was kept cold and basified with solid $K_2CO_3$ to pH 8–9. The resulting crude free base was suspended in methanol and converted to the hydrochloride salt by addition of ethereal HCl. The resulting clear solution was treated with charcoal and filtered through diatomaceous earth. The filtrate was evaporated to dryness in vacuo and the residue crystallized from MeOH/2-PrOH two times to yield the pure product, 3.05 g (18.5%), m.p. 202.5°–204.5° C., as a white solid.

Anal. Calc'd for $C_{10}H_{10}Cl_2N_4O \cdot HCl \cdot 1/16 H_2O$: C, 38.66; H, 3.61; N, 18.03; Cl, 34.23; $H_2O$, 0.36; Found: C, 38.71; H, 3.56; N, 17.86; Cl, 34.13; $H_2O$, 0.34.

EXAMPLE 7

2-Amino-N-(2,5-dichlorophenyl)-4,5-dihydro-1H-imidazole-1-carboxamide Monohydrochloride

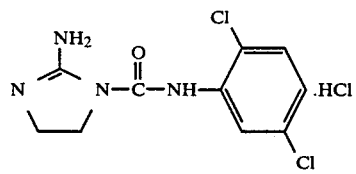

A suspension of 2.13 g (0.268 mole) of lithium hydride in 80 ml of dry DMF was treated under $N_2$ with a solution of 57.1 g (0.268 mole) of 2-iminoimidazolidine monohydroiodide in 65 ml of dry DMF dropwise so that temperature did not exceed +25° C.; stirred for 2 hours, then cooled to −20° C. and added a solution of 25.27 g (0.134 mole) of 2,5-dichlorophenyl isocyanate in 40 mls of dry DMF slowly dropwise over a 2-hour period, not allowing the temperature to go above −20° C.; stirred at −20° C. for an additional 1 hour, then stored in a freezer at −25° C. overnight. The reaction mixture was allowed to warm to room temperature for 1½ hours, divided into two equal portions, and one portion worked up as follows to obtain the product: the mixture was cooled in ice/$H_2O$ and 10% HCl was added to pH <3. The resulting white precipitate was poured onto 800 ml of ice/$H_2O$, stirred and filtered. The filtrate was kept cold in ice and basified with solid $K_2CO_3$ to pH 8–9. The crude white base was filtered, washed with water, and immediately suspended in 100 ml of methanol and added excess ethereal HCl (pH <3) to dissolve. The solvent and excess HCl were removed in vacuo to yield the crude product which was recrystallized from methanol/ether one time, then recrystallized from methanol/2-propanol to give nearly pure product (was contaminated with water-soluble inorganics). The hydrochloride was reconverted to the free base in water (cold) by basification to pH 8–9 with solid $K_2CO_3$. This was dissolved in MeOH/ethereal HCl as above, filtered some cloudiness, and concentrated in vacuo to give the hydrochloride salt again. Recrystallized one time from methanol/ether to yield 4.2 g (20.2%) of pure product, m.p. 202°–204° C. (252°–254° C.).

Anal. Calc'd for $C_{10}H_{10}Cl_2N_4O \cdot HCl$: C, 38.80; H, 3.58; N, 18.10; Cl, 34.35; Found: C, 38.73; H, 3.57; N, 18.19; Cl, 34.18.

EXAMPLE 8

2-Amino-N-(3,4-dichlorophenyl)-4,5-dihydro-1H-imidazole-1-carboxamide Monohydrochloride Monohydrate, Compound with 1,1'Oxybisethane (12:1)

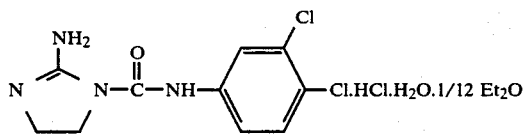

A suspension of 2.13 g (0.268 mole) of lithium hydride in 100 ml of dry DMF was treated with a solution of 57.1 g (0.2 mole) of 2-iminoimidazolidine monohydroiodide in 75 ml of dry DMF (under $N_2$) dropwise so that temperature did not exceed +30° C.; stirred until all was homogeneous (2 hours) then cooled to −10° C. and added slowly dropwise a solution of 25.3 g (0.134 mole) of 3,4-dichlorophenylisocyanate in 75 ml of dry DMF over a 2-hour period. Maintained a temperature of −10° to −13° C. throughout the addition and stirred at −10° to −15° for 3 more hours. Stored the reaction mixture in the refrigerator at +4° C. overnight. Allowed to warm to +10° C. then placed in ice/$H_2O$ bath and acidified to pH <3 with 10% HCl. Added to 1400 ml of ice/$H_2O$ and stirred. Filtered some insoluble material and the filtrate basified with solid $K_2CO_3$ (keep cold!) to pH 8–9. Filtered the resulting white solid, the free base of the product. Immediately suspended in 200 ml of MeOH and dissolved by addition of ethereal HCl to pH <3. The solvent and excess HCl were removed in vacuo to yield the crude product, a white solid. The free base was regenerated again as above and converted to the hydrochloride as before. Several recrystallizations resulted in the pure product being isolated from a mixture of MeOH/$H_2O$/$Et_2O$ as a white solid, 4.08 g (18.2%), m.p. 210°–212° C. [Compound is sensitive to heat; above 50°/vac may lose HCl].

Anal. Calc'd for $C_{10}H_{10}Cl_2N_4O \cdot HCl \cdot H_2O \cdot 1/12 Et_2O$: C, 37.22; H, 4.08; N, 16.80; Cl, 31.90; $H_2O$, 5.52 Found: C, 37.26; H, 4.34; N, 16.74; Cl, 31.63; $H_2O$, 5.40.

EXAMPLE 9

2-Amino-N-(2,4-dichlorophenyl)-4,5-dihydro-1H-imidazole-1-carboxamide Monohydrochloride

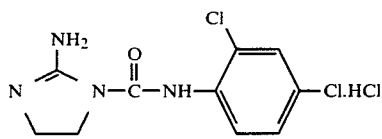

The title compound was prepared by Method B. The crude salt was purified by recrystallization from MeOH/2-PrOH to yield the purified product, a white solid, m.p. 210°–212° C.

Anal. Calc'd for $C_{10}H_{10}Cl_2N_4O \cdot HCl$: C, 38.80; H, 3.58; N, 18.10; Cl, 34.35; Found: C, 38.84; H, 3.69; N, 17.91; Cl, 34.43.

EXAMPLE 10

2-Amino-N-(2,3-dichlorophenyl)-4,5-dihydro-1H-imidazole-1-carboxamide Monohydrochloride

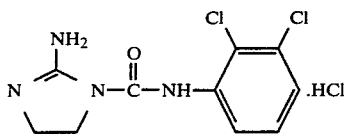

The title compound was prepared by Method B. The crude salt was purified by recrystallization from MeOH/Et$_2$O to yield the purified product, a white solid, m.p. 209°–211° C.

Anal. Calc'd for $C_{10}H_{10}Cl_2N_4O \cdot HCl$: C, 38.80; H, 3.58; N, 18.10; Cl, 34.36; Found: C, 38.49; H, 3.54; N, 17.93; Cl, 34.47.

EXAMPLE 11

2-Amino-N-(3-chlorophenyl)-4,5-dihydro-1H-imidazole-1-carboxamide Monohydrochloride Monohydrate

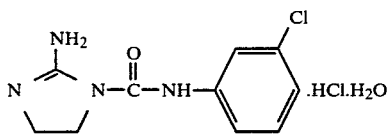

The title compound was prepared by Method B. The crude salt was recrystallized from MeOH/Et$_2$O to yield the purified product, a white solid, m.p. 188°–190° C.

Anal. Calc'd for $C_{10}H_{11}ClN_4O \cdot HCl \cdot H_2O$: C, 40.97; H, 4.81; N, 19.11; Cl, 24.19; H$_2$O, 6.14; Found: C, 40.82; H, 4.80; N, 19.01; Cl, 24.24; H$_2$O, 6.08.

EXAMPLE 12

2-Amino-4,5-dihydro-N-(2,4,6-trichlorophenyl)-1H-imidazole-1-carboxamide Monohydrochloride

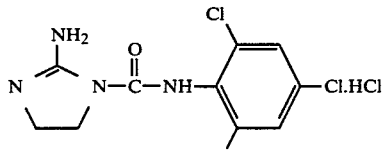

The title compound was prepared by Method B. The crude salt was recrystallized from MeOH/2-PrOH to yield the purified product, a white solid, m.p. 210° C. (255° C. dec.).

Anal. Calc'd for $C_{10}H_9Cl_3N_4O \cdot HCl$: C, 34.91; H, 2.93; N, 16.29, Cl, 41.22; Found: C, 34.86; H, 3.04; N, 16.07; Cl, 41.12.

EXAMPLE 13

N-2-Imidazolidinylidene-N'-(2,4,6-trimethylphenyl)urea Monohydrochloride

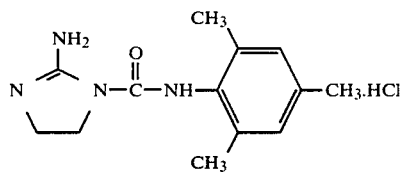

A suspension of 25.56 g (0.12 mole) of 2-iminoimidazolidine monohydroiodide in 400 ml of THF was treated with 9.6 g (0.12 mole) of 50% sodium hydroxide solution and stirred for ½ hour. The resulting clear solution was treated with 18 g of anhydrous sodium sulfate and stirred (under N$_2$) for an additional ½ hour. The mixture was then cooled to −20° C. and a solution of 9.67 g (0.06M) of 2,4,6-trimethylphenyl isocyanate in 150 ml of dry THF added dropwise over a 2½-hour period while stirring at −20° C. Stirred an additional 2 hours at −20°, then filtered off inorganics. The filtrate was concentrated in vacuo (pump) keeping cold throughout [this particular compound must be handled with extreme care (COLD!) while in the free base form]. The residue, a yellow oil, was dissolved in 500 ml cold CH$_2$Cl$_2$ and washed with 200 ml cold brine. The CH$_2$Cl$_2$ phase was dried over anhydrous K$_2$CO$_3$ then treated with excess ethereal HCl (pH <3). The solvent and excess HCl were removed in vacuo to yield a white solid. This was dissolved in 100 ml of fresh MeOH and diluted to the cloud point with ether (500 ml) and allowed to crystallize overnight at room temperature. Filtered 14.9 g (87.8%) of crude product, m.p. 209°–211° (dec.). The crude material was recrystallized from MeOH/2-PrOH, then twice from MeOH/Et$_2$O to yield 9.3 g (54.8%) of pure product, a white solid, m.p. 210°–212° C. (dec.) which forms a new solid that decomposes at 298° C.

Anal. Calc'd for $C_{13}H_{18}N_4O \cdot HCl$: C, 55.22; H, 6.77; N, 19.81; Found: C, 55.17; H, 6.80; N, 19.83.

EXAMPLE 14

2-Amino-4,5-dihydro-N-(4-trifluoromethylphenyl)-1H-imidazole-1-carboxamide Monohydrochloride

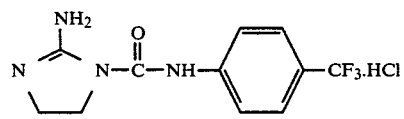

A suspension of 25.6 g (0.12M) of 2-iminoimidazolidine monohydroiodide in 300 ml of THF was stirred with 9.6 g (0.12M) of 50% NaOH for 15 minutes. The clear solution was treated with 20 g anhydrous Na$_2$SO$_4$ and stirred another ½ hour. The inorganics were removed by filtration and the filtrate cooled to −20° C. A solution of 14.17 g (0.06M) of 4-trifluoromethylphenyl isocyanate in 75 ml of THF was added slowly dropwise while stirring at −20° C. over a 2½ hour period. The clear solution was stirred an additional 1½ hour, stoppered, and stored overnight at −26° C. The solvent was removed in vacuo at <10° C. and the residue extracted into 1 l CHCl₃ and washed with 2×150 ml H₂O. The organic phase dried (K₂CO₃) and filtered. The filtrate was treated with excess ethereal HCl (pH <3) and concentrated in vacuo to yield the crude hydrochloride salt. This was mostly dissolved in 200 ml MeOH and filtered to remove some insoluble material. The filtrate was concentrated in vacuo to yield an amber gum. This was dissolved in 40 ml fresh MeOH and diluted to the cloud point (1 l) with Et₂O, filtered, to yield 8.5 g of white solid, the crude product. One recrystallization from MeOH/acetone followed by another from MeOH/Et₂O yielded 4.8 g (25.9%) of the pure product, a white solid, m.p. 210°–212° C.

Anal. Calc'd for $C_{11}H_{11}F_3N_4O \cdot HCl$: C, 42.80; H, 3.92; N, 18.15; Found: C, 42.70; H, 3.96; N, 18.16.

EXAMPLE 15

2-Amino-N-(2-chloro-6-methylphenyl)-4,5-dihydro-1H-imidazole-1-carboxamide Monohydrochloride Hydrate (8:1)

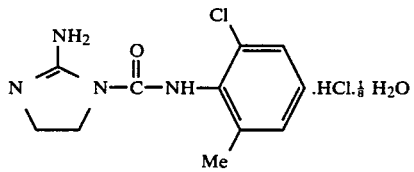

A suspension of 25.56 g (0.2M) of 2-iminoimidazolidine monohydroiodide in 500 ml of THF was treated with 9.6 g (0.2M) of 50% NaOH solution and stirred for ½ hour. Added 20 g of anhydrous Na₂SO₄ and stirred another ½ hour. Cooled to −20° C. (it was necessary to maintain a temperature of −20° C. at all times while this compound was in the free base form to avoid isomerization to the 2-isomer) under N₂ and added a solution of 10.1 g (0.1M) of 2-chloro-6-methylphenyl isocyanate in 150 ml THF dropwise while stirring over a 3-hour period, keeping the temperature at −20° C. Stirred another 2 hours at −20° C. and filtered off inorganics. The filtrate was evaporated cold in vacuo (pump) to yield a yellow oil. This was stirred in 200 ml of brine at −30° C. and 2×250 ml cold CH₂Cl₂. The organic phases were separated and dried over anhydrous K₂CO₃ and filtered. The filtrate was treated with cold excess ethereal HCl and an oil formed. The solvent and excess HCl were removed in vacuo and the residue crystallized from MeOH/Et₂O to yield 14 g (80.7%) of nearly pure product. This was recrystallized from MeOH/2-PrOH then from MeOH/Et₂O to yield 9.9 g (57.1%) of pure hydrochloride salt, a white solid, m.p. 196°–198° C. that decomposes to a new solid melting at 264°–268° C.

Anal. Calc'd for $C_{11}H_{13}N_4OCl \cdot HCl \cdot 1/8 H_2O$: C, 45.34; H, 4.93; N, 19.23; H₂O, 0.77; Found: C, 45.01; H, 4.84; N, 19.03; H₂O, 0.53.

EXAMPLE 16

2-Amino-4,5-dihydro-N-(2,6-dibromophenyl)-1H-imidazole-1-carboxamide Monohydrochloride

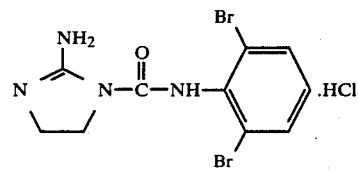

A suspension of 21.30 g (0.1 mole) of 2-iminoimidazolidine monohydroiodide in 250 ml THF was treated with 8 g (0.1 mole) 50% NaOH solution and stirred for 0.5 hour. Ten grams of anhydrous Na₂SO₄ were added and the mixture stirred 0.5 hour more. After cooling to −20° C. (it was necessary to maintain a temperature of −20° C. at all times to prevent isomerization) under N₂, a solution of 13.85 g (0.05 mole) of 2,6-dibromophenyl isocyanate in 200 ml THF was added dropwise over a 3-hour period, maintaining a temperature of −20° C. The mixture was stirred an additional 45 minutes and then the inorganics were filtered and the filtrate was evaporated cold, in vacuo, to leave a yellow oil which was stirred in 250 ml cold brine and extracted with 3×150 ml cold CH₂Cl₂. The CH₂Cl₂ extracts were dried over K₂CO₃, filtered, and the filtrate treated with cold ethereal HCl to pH <3 and a white solid formed. The mixture was stored in a freezer overnight. The acidic solvent was decanted from a gummy residue and was evaporated to leave a yellow solid. Et₂O was added to the gum, the mixture acidified with additional anhydrous HCl, and MeOH added to dissolve the residue. This was evaporated to leave a yellow solid. The combined yield of crude product was 19.09 g (95.8%) which, after repeated purification and a final recrystallization from MeOH/Et₂O, yielded 6.5 g (32.6%) of pure hydrochloride salt, a white solid, m.p. 240.5°–243° C. (initially melted at 220° C. then decomposing to form the higher melting solid).

Anal. Calc'd for $C_{10}H_{10}Br_2N_4O \cdot HCl$: C, 30.14; H, 2.78; N, 14.06; Found: C, 30.08; H, 2.84; N, 14.02.

EXAMPLE 17

2-Amino-4,5-dihydro-N-(2-ethyl-6-methylphenyl)-1H-imidazole-1-carboxamide Monohydrochloride

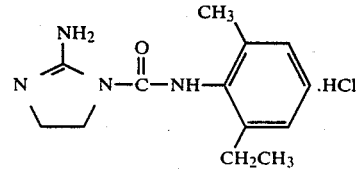

A suspension of 42.6 g (0.2 mole) of 2-iminoimidazolidine monohydroiodide in 500 ml THF was treated with 16 g (0.2 mole) 50% NaOH solution and stirred for 0.5 hour. Twenty grams of anhydrous Na₂SO₄ were added and the mixture was stirred 0.5 hour more. After cooling to −20° C. (it was necessary to maintain a temperature of −20° C. at all times to avoid isomerization) under N₂, a solution of 16.12 g (0.1 mole) of 2-ethyl-6-methylphenyl isocyanate in 125 ml THF was added dropwise while stirring, maintaining a temperature of −20° C. The mixture was stirred an additional hour then the solvent was removed in vacuo, cold, to yield a yellow oil which was stirred in cold brine and extracted 3×150 ml CH$_2$Cl$_2$, keeping everything cold. The CH$_2$Cl$_2$ extracts were dried over anhydrous K$_2$CO$_3$ and filtered. The cold filtrate was treated with cold, excess ethereal HCl to pH <3, and MeOH was added to dissolve. The solution was stored in a freezer overnight and the solvent was removed in vacuo to leave a yellow residue which solidified after washing with Et$_2$O to yield 25.49 g (90.1%) crude product which was recrystallized from MeOH/Et$_2$O, washed with 2-PrOH to yield nearly pure product, and recrystallized from MeOH/Et$_2$O to yield 13.25 g (46.9%) of pure hydrochloride salt, m.p. 194.5°–197° C., a white solid.

Anal. Calc'd for C$_{13}$H$_{18}$N$_4$O.HCl: C, 55.22; H, 6.77; N, 19.81; Found: C, 55.22; H, 6.93; N, 19.89.

EXAMPLE 18

2-Amino-4,5-dihydro-N-(2-methoxyphenyl)-1H-imidazole-1-carboxamide Monohydrochloride Hydrate (5:1)

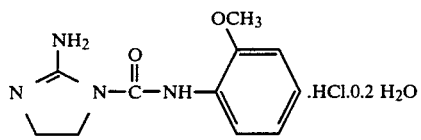

A suspension of 42.6 g (0.2 mole) of 2-iminoimidazolidine monohydroiodide in 500 ml THF was treated with 16 g (0.2 mole) 50% NaOH solution and stirred for 0.5 hour. Twenty grams of anhydrous Na$_2$SO$_4$ were added and the mixture stirred an additional 0.5 hour. After cooling to −20° C. (it was necessary to maintain a temperature of −20° C. at all times to prevent isomerization) under N$_2$, a solution of 14.92 g (0.1 mole) of 2-methoxyphenyl isocyanate in 100 ml THF was added dropwise to the reaction mixture over a 3-hour period maintaining a −20° C. temperature. The mixture was stirred an additional 0.5 hour and the inorganics were filtered and the filtrate was evaporated in vacuo, cold, to yield a yellow oil which was stirred in brine and extracted 3×150 ml CH$_2$Cl$_2$. The CH$_2$Cl$_2$ extracts were dried over anhydrous K$_2$CO$_3$ and filtered. The filtrate was acidified to pH <3 using cold ethereal HCl and MeOH was added to make a solution, which was stored in a freezer overnight. The solvent was evaporated to yield a yellow oil which solidified when washed with Et$_2$O, to give crude product which was recrystallized from MeOH/Et$_2$O, and then MeOH/2-PrOH to yield 16.37 g (60.5%) of pure hydrochloride salt, m.p. 189.5°–193° C. (dec.).

Anal. Calc'd for C$_{11}$H$_{14}$N$_4$O$_2$.HCl.0.2H$_2$O: C, 48.16; H, 5.66; N, 20.42; H$_2$O, 1.31; Found: C, 48.46; H, 5.66; N, 20.57; H$_2$O, 1.39.

EXAMPLE 19

2-Amino-4,5-dihydro-N-(3-methoxyphenyl)-1H-imidazole-1-carboxamide Monohydrochloride Hydrate (5:1)

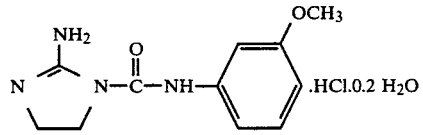

A suspension of 42.6 g (0.2 mole) of 2-iminoimidazolidine monohydroiodide in 500 ml THF was treated with 16 g (0.2 mole) 50% NaOH solution and stirred for 0.5 hour. Twenty grams of anhydrous Na$_2$SO$_4$ were added and the mixture was stirred an additional 0.5 hour. After cooling to −20° C. (it was necessary to maintain −20° C. to prevent isomerization) under N$_2$, 14.92 g (0.1 mole) 3-methoxyphenyl isocyanate in 125 ml THF was added dropwise over a 3-hour period, maintaining a −20° C. temperature. The mixture was stirred an additional 0.5 hour, then the inorganics were filtered off and the filtrate was evaporated cold, in vacuo, to yield a yellow oil, which was stirred in brine and extracted with 3×150 ml CH$_2$Cl$_2$, keeping the solvents cold. The combined CH$_2$Cl$_2$ extracts were dried over K$_2$CO$_3$ and filtered. The filtrate was treated with cold, excess ethereal HCl to pH <3, adding MeOH to maintain a solution, which was stored in a freezer overnight. The solvent and excess HCl were removed in vacuo and the yellow-white solid remaining was washed with Et$_2$O, then recrystallized from MeOH/Et$_2$O to yield 19.1 g (70.6%) of crude product which was again recrystallized from MeOH/Et$_2$O to yield 12.54 g (46.32%) pure hydrochloride salt, m.p. 186°–187.5° C. (dec.), a white solid.

Anal. Calc'd for C$_{11}$H$_{14}$N$_4$O$_2$.HCl.0.2H$_2$O: C, 48.16; H, 5.66; N, 20.42; H$_2$O, 1.31; Found: C, 48.27; H, 5.70; N, 20.33; H$_2$O, 1.31.

EXAMPLE 20

2-Amino-4,5-dihydro-N-(4-methoxyphenyl)-1H-imidazole-1-carboxamide Monohydrochloride

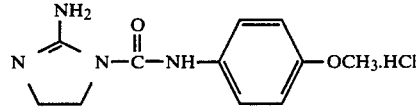

A suspension of 21.3 g (0.1 mole) of 2-iminoimidazolidine.HI in 250 ml THF was treated with 8 g (0.1 mole) of 50% NaOH solution and stirred for 0.5 hour. Ten grams of anhydrous Na$_2$SO$_4$ were added and the mixture stirred another 0.5 hour. After cooling to −20° C. (it was necessary to maintain a temperature of −20° C. at all times while compound was in free base form to avoid isomerization) under N$_2$, 7.45 g (0.05 mole) of 4-methoxyphenyl isocyanate in 60 ml THF was added dropwise over a 2.5-hour period, maintaining −20° C. The mixture was stirred an additional hour, then the inorganics were filtered off and the solvent was removed in vacuo, cold, to yield a yellow oil, which was stirred in 200 ml cold brine and extracted with 3×100 ml portions of cold CH$_2$Cl$_2$. The CH$_2$Cl$_2$ extracts were dried over anhydrous K$_2$CO$_3$, filtered, and the filtrate was acidified to pH <3 with cold excess ethereal HCl, adding MeOH to dissolve any solid which formed. The solution was stored in a freezer overnight. The solvent and excess HCl were removed in vacuo to yield 11.40 g of a yellow-white solid, which was recrystallized from MeOH/Et$_2$O, converted to the free base and back to the HCl salt, and, finally, recrystallized from MeOH/Et$_2$O to yield 3.24 g of pure hydrochloride salt, m.p. 199°–201° C. (dec.), a white solid.

Anal. Calc'd for C$_{11}$H$_{14}$N$_4$O$_2$.HCl: C, 48.80; H, 5.58; N 20.70; Found: C, 48.74; H, 5.60; N, 20.66.

EXAMPLE 21

2-Amino-4,5-dihydro-N-(2,6-dimethoxyphenyl)-1H-imidazole-1-carboxamide Monohydrochloride

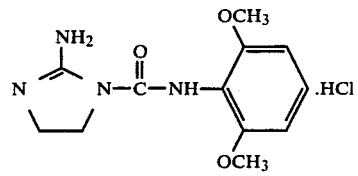

A suspension of 21.3 g (0.1 mole) of 2-iminoimidazolidine monohydroiodide in 250 ml THF was treated with 8.0 g (0.1 mole) of 50% NaOH solution and stirred for 0.5 hour. Ten grams of anhydrous $Na_2SO_4$ were added and the mixture stirred for 0.5 hour. After cooling to $-20°$ C. (it was necessary to maintain a temperature of $-20°$ C. at all times to avoid isomerization) under $N_2$, a solution of 8.96 g (0.05 mole) of 2,6-dimethoxyphenyl isocyanate in 110 ml THF was added dropwise over a $2\frac{1}{2}$-hour period, maintaining the temperature at $-20°$ C. The reaction was stirred an additional hour after the addition, then the solvent was removed in vacuo, cold, to yield a yellow oil, which was stirred in brine and extracted with $3 \times 150$ ml portions of cold $CH_2Cl_2$. The $CH_2Cl_2$ extracts were dried over anhydrous $K_2CO_3$ and filtered. The filtrate was treated with ethereal HCl (excess) to pH <3, adding methanol, to maintain a clear solution. The solution was stored in a freezer overnight. The solvent was removed in vacuo to leave a yellow oil, which was washed with $Et_2O$ and scratched until it solidified to yield 12.91 g (85.8%) of crude product, which was recrystallized from $MeOH/Et_2O$, then $MeOH/2$-PrOH to yield 5.51 g (36.6%), which was converted to the free base and back to the hydrochloride salt, and finally recrystallized from $MeOH/Et_2O$ to yield 3.36 g (22.3%) of pure hydrochloride salt, a white solid, m.p., 199°–199.5° C.

Anal. Calc'd for $C_{12}H_{16}N_4O_3 \cdot HCl$: C, 47.93; H, 5.70; N, 18.63; Found: C, 47.73; H, 5.77; N, 18.45.

EXAMPLE 22

2-Amino-4,5-dihydro-N-(3-methylphenyl)-1H-imidazole-1-carboxamide Monohydrochloride

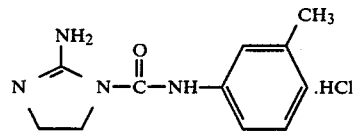

A suspension of 31.95 g (0.15 mole) of 2-iminoimidazolidine monohydroiodide in 400 ml THF was treated with 11.99 g (0.15 mole) 50% NaOH solution and stirred for 0.5 hour. Twenty grams of anhydrous $Na_2SO_4$ were added and the mixture stirred an additional 0.5 hour. After cooling to $-20°$ C. (it was necessary to maintain a temperature of $-20°$ C. at all times when in the free base form) under $N_2$, a solution of 9.99 g (0.075 mole) of 3-methylphenyl isocyanate in 125 ml THF was added dropwise over a 3-hour period, maintaining a temperature of $-20°$ C. The mixture was stirred an additional hour, then the inorganics were filtered off and the solvent was removed in vacuo, cold, to yield a yellow oil, which was stirred in cold brine and extracted with $3 \times 150$ ml portions of cold $CH_2Cl_2$. The combined $CH_2Cl_2$ extracts were dried over anhydrous $K_2CO_3$ and filtered. The filtrate was acidified to pH <3 with excess ethereal HCl, adding MeOH to dissolve solids which formed upon acidification. The solution was stored in a freezer overnight. The solvent and excess HCl were removed in vacuo to leave a yellow-orange oil, which solidified when washed with $Et_2O$. The solid was recrystallized from $MeOH/Et_2O$ to yield 11.11 g of impure product which was converted to the free base and then back to the HCl salt, and recrystallized from $MeOH/Et_2O$ to yield 7.99 g (41.8%) of pure hydrochloride salt, a white solid, m.p. 195°–196.5° C. (dec.).

Anal. Calc'd for $C_{11}H_{14}N_4O \cdot HCl$: C, 51.87; H, 5.94; N, 22.00; Found: C, 51.67; H, 5.98; N, 21.86.

EXAMPLE 23

2-Amino-4,5-dihydro-N-phenyl-1H-imidazole-1-carboxamide Monohydrochloride Hydrate (5:3)

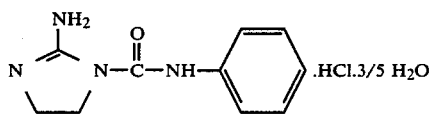

A suspension of 31.95 g (0.15 mole) of 2-iminoimidazolidine monohydroiodide in 400 ml THF was treated with 11.99 g (0.15 mole) of 50% NaOH solution and stirred for 0.5 hour. Ten grams of anhydrous $Na_2SO_4$ were added and the mixture stirred an additional 0.5 hour. After cooling to $-20°$ C. (it was necessary to maintain a temperature of $-20°$ C. while compound was in free base form to avoid isomerization) under $N_2$, a solution of 8.94 g (0.075 mole) of phenyl isocyanate in 125 ml THF was added dropwise over a 3-hour period. The mixture was stirred an additional 45 minutes, then the inorganics were filtered off, and the solvent was removed in vacuo, cold, to yield a yellow oil which was stirred in 250 ml cold brine and extracted with $3 \times 150$ ml portions of cold $CH_2Cl_2$. The combined $CH_2Cl_2$ extracts were dried over anhydrous $K_2CO_3$ and filtered. The filtrate was acidified to pH <3 with excess ethereal HCl adding MeOH to dissolve any solid that formed. The solution was stored in a freezer overnight. The solvent and excess HCl were removed in vacuo to yield a gummy yellow solid which was washed several times with $Et_2O$, then recrystallized from $MeOH/Et_2O$ to yield 8.12 g (45%) of crude product which was recrystallized twice from $MeOH/Et_2O$ to yield 5.43 g (30.1%) of pure hydrochloride salt, m.p. 189.5°–193° C. (dec.), a white solid.

Anal. Calc'd for $C_{10}H_{12}N_4O \cdot HCl \cdot 0.6H_2O$: C, 47.76; H, 5.69; N, 22.28; $H_2O$, 4.30; Found: C, 48.13; H, 5.64; N, 22.44; $H_2O$, 4.05.

EXAMPLE 24

2-Amino-4,5-dihydro-N-(2-methylphenyl)-1H-imidazole-1-carboxamide Monohydrochloride

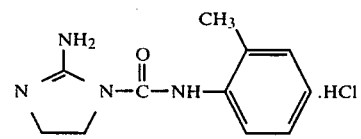

A suspension of 31.95 g (0.15 mole) of 2-iminoimidazolidine monohydroiodide in 400 ml THF was treated with 11.99 g (0.15 mole) of 50% NaOH solution and stirred for 0.5 hour. Ten grams of anhydrous $Na_2SO_4$ were added and the mixture was stirred another 0.5 hour. The mixture was cooled to $-20°$ C. (it was necessary to maintain a temperature of $-20°$ C. at all times while compound was in free base form to avoid isomerization) under $N_2$ and a solution of 9.99 g (0.075 mole) of 2-methylphenyl isocyanate in 125 ml THF was added dropwise over a 3-hour period. The reaction was stirred an additional hour at $-20°$ C. and the inorganics were filtered off and the solvent was removed in vacuo, cold, to yield a yellow oil which was stirred in cold brine and extracted with $3 \times 150$ ml portions of cold $CH_2Cl_2$. The $CH_2Cl_2$ extracts were dried over anhydrous $K_2CO_3$ and filtered. The filtrate was acidified to pH <3 with excess ethereal HCl, adding MeOH to dissolve any solids that formed. The solution was stored in a freezer overnight. The solvent and excess HCl were removed in vacuo and the yellow oil was washed with $Et_2O$ and solidified. Recrystallization from $MeOH/Et_2O$ yielded 13.48 g (70.6%) of nearly pure product, which was recrystallized twice from $MeOH/Et_2O$ to yield 10.46 g (54.8%) of pure hydrochloride salt, m.p. 183.5°–185° C. (dec.), a white solid.

Anal. Calc'd for $C_{11}H_{14}N_4O.HCl$: C, 51.87; H, 5.93; N, 22.00; Found: C, 51.85; H, 5.93; N, 22.06.

EXAMPLE 25

2-Amino-4,5-dihydro-N-(2-trifluoromethylphenyl)-1H-imidazole-1-carboxamide Monohydrochloride

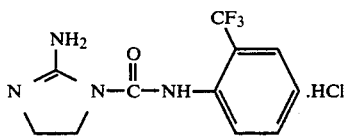

A suspension of 42.60 g (0.2 mole) of 2-iminoimidazolidine monohydroiodide in 500 ml THF was treated with 16 g (0.2 mole) of 50% NaOH solution and stirred for 0.5 hour. Twenty grams of anhydrous $Na_2SO_4$ were added and the mixture stirred for another 0.5 hour. The mixture was cooled to $-20°$ C. (it was necessary to maintain a temperature of $-20°$ C. at all times to avoid isomerization) under $N_2$ and a solution of 18.71 g (0.1 mole) 2-trifluoromethylphenyl isocyanate in 125 ml THF was added dropwise while stirring over a 3-hour period, maintaining the temperature at $-20°$ C. The mixture sitrred for another hour at $-20°$ C. then the inorganics were filtered off and the solvent was removed cold, in vacuo, to yield a yellow-green oil, which was stirred in cold brine and extracted with $3 \times 150$ ml portions of cold $CH_2Cl_2$. The combined $CH_2Cl_2$ extracts were dried over anhydrous $K_2CO_3$ and filtered. The filtrate was acidified with cold, excess ethereal HCl to pH <3 and was stored in a freezer overnight. The solvent and excess HCl was removed in vacuo and the yellow solid remaining was washed with $Et_2O$ to remove excess HCl. The solid (25.2 g; 81.6%) was recrystallized from $MeOH/Et_2O$ to yield 17.2 g (55.7%) of impure product, which was recrystallized from $MeOH/2-PrOH/Et_2O$, and finally from $MeOH/Et_2O$ to yield 4.7 g (15.2%) of pure hydrochloride salt, m.p. 166.5°–167° C. (dec.), a white solid.

Anal. Calc'd for $C_{11}H_{11}F_3N_4O.HCl$: C, 42.80; H, 3.92; N 18.15; Found: c, 42.69; H, 4.09; N, 18.13.

EXAMPLE 26

2-Amino-4,5-dihydro-N-(3-trifluoromethylphenyl)-1H-imidazole-1-carboxamide Monohydrochloride Hemihydrate

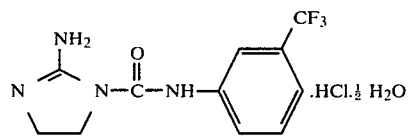

A suspension of 42.60 g (0.2 mole) of 2-iminoimidazolidine monohydroiodide in 500 ml THF was treated with 16 g (0.2 mole) of 50% NaOH solution and stirred for 0.5 hour. Twenty grams of anhydrous $Na_2SO_4$ were added and the reaction stirred for another 0.5 hour. The mixture was cooled to $-20°$ C. (it was necessary to maintain a temperature of $-20°$ C. while the compound was in the free base form to avoid isomerization) under $N_2$ and a solution of 18.71 g (0.1 mole) of 3-trifluoromethylphenyl isocyanate in 125 ml THF was added dropwise while stirring over a 3-hour period, maintaining a temperature of $-20°$ C. The reaction stirred another hour at $-20°$ C., the inorganics were filtered off and the filtrate was evaporated cold, in vacuo, to yield a yellow oil. This was stirred in 250 ml brine at $-20°$ C. and extracted with $2 \times 250$ ml portions of cold $CH_2Cl_2$. The $CH_2Cl_2$ extracts were dried over anhydrous $K_2CO_3$ and filtered, keeping the filtrate cold. The filtrate was treated with cold excess ethereal HCl and a solid formed. The mixture was left in a freezer overnight and then the solvent and excess HCl were removed in vacuo and the solid residue was washed with $Et_2O$ to remove excess HCl. The solid residue was recrystallized from $MeOH/Et_2O$ to yield 16.3 g (52.8%) of crude product, which was recrystallized from $MeOH/2-PrOH$, and finally from 2-PrOH to yield 4.98 g (16.1%) pure hydrochloride salt, m.p. 174°–177° C. (dec.), a white solid.

Anal. Calc'd for $C_{11}H_{11}F_3N_4O.HCl.\frac{1}{2}H_2O$: C, 41.59; H, 4.12; N, 17.64; $H_2O$, 2.83; Found: C, 41.77; H, 4.23; N 17.56; $H_2O$, 2.74.

EXAMPLE 27

2-Amino-N-(4-chlorophenyl)-4,5-dihydro-1H-imidazole-1-carboxamide Monohydrochloride Hydrate (17:1)

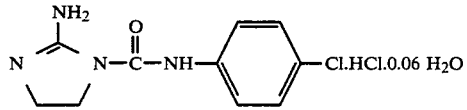

A mixture of 25.56 g (0.2 mole) of 2-iminoimidazolidine monohydroiodide in 400 ml of anhydrous THF and 16 g (0.2 mole) of 50% NaOH solution was stirred under $N_2$ for 30 minutes. After adding 18 g of anhydrous $Na_2SO_4$ and stirring for 30 minutes, the mixture was cooled to $-20°$ C. and a solution of 9.21 g (0.06 mole) of 4-chlorophenyl isocyanate in 150 ml THF was added dropwise (2 hours, 40 minutes) to the stirred mixture. The mixture was stirred an additional 2 hours at $-20°$ C. It was then evaporated in vacuo keeping the temperature between 8°–15° C. Cold $CH_2Cl_2$ was added to the mixture and was washed with cold brine. The brine solution was washed once with cold $CH_2Cl_2$, the organic layer dried over anhydrous $K_2CO_3$ and filtered.

Cold Et₂O/HCl was added (pH=3) and an oil formed. The solvent was removed in vacuo keeping the temperature below 30° C. Methanol was added to the oil and warmed to dissolve. Ether was added to the cloud point and the mixture allowed to crystallize at room temperature. This solid was recrystallized twice from MeOH/Et₂O to yield 4.05 g of white solid, m.p. 201°–202° C. (corr.).

Anal. Calc'd for C₁₀H₁₁ClN₄O.HCl.0.06H₂O: C, 43.48; H, 4.42; Cl, 25.67; H₂O, 0.39; Found: C, 43,72; H, 4.45; Cl, 25.31; H₂O, 0.38.

In operations carried out in a manner similar to that described in general method "A" or "B" but using appropriate analogous reactants, the following compounds may also be prepared:

2-amino-N-(2-ethoxyphenyl)-4,5-dihydro-1H-imidazole-1-carboxamide monohydrochloride.
2-amino-4,5-dihydro-N-[4-(methylthio)phenyl]-1H-imidazole-1-carboxamide monohydrochloride.
2-amino-4,5-dihydro-N-(2,6-dimethyl-4-fluorophenyl)-1H-imidazole-1-carboxamide monohydrochloride.
2-amino-N-(2,6-difluorophenyl)-4,5-dihydro-1H-imidazole-1-carboxamide monohydrochloride.
2-amino-N-(2-chloro-6-methoxyphenyl)-4,5-dihydro-1H-imidazole-1-carboxamide monohydrochloride.
2-amino-N-(2-chloro-6-trifluoromethylphenyl)-4,5-dihydro-1H-imidazole-1-carboxamide monohydrochloride.
2-amino-4,5-dihydro-N-(2-methoxy-6-trifluoromethylphenyl)-1H-imidazole-1-carboxamide monohydrochloride.
2-amino-4,5-dihydro-N-(2-methyl-6-trifluoromethylphenyl)-1H-imidazole-1-carboxamide monohydrochloride.
2-amino-N-(2,6-bistrifluoromethylphenyl)-4,5-dihydro-1H-imidazole-1-carboxamide monohydrochloride.
2-amino-4,5-dihydro-N-(2-methoxy-6-methylphenyl)-1H-imidazole-1-carboxamide monohydrochloride.

I claim:

1. A process for preparing an acid addition salt of a compound of the following formula (I) which is stable to rearrangement

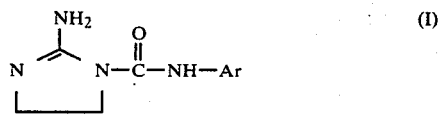

wherein
Ar is phenyl substituted with from 0 to 3 substituents independently selected from the group consisting of fluoro, chloro, bromo, methyl, ethyl, methoxy, ethoxy, trifluoromethyl and methylthio, which comprises:
(i) reacting 2-iminoimidazolidine with an appropriate aryl isocyanate of the formula ArNCO at a temperature of about −10° to −20° C.;
(ii) reacting the free base resulting from step (i) with an appropriate acid; and
(iii) isolating the acid addition salt product of step (ii).

* * * * *